US00PP07998P

United States Patent [19]

van der Knaap

[11] Patent Number: Plant 7,998

[45] Date of Patent: Oct. 6, 1992

[54] CHRYSANTHEMUM PLANT — CREAM DAYMARK CULTIVAR

[75] Inventor: Jacques C. M. van der Knaap, De Lier, Netherlands

[73] Assignee: Fides Beheer B.V., De Lier, Netherlands

[21] Appl. No.: 577,750

[22] Filed: Sep. 5, 1990

[51] Int. Cl.[5] ..... A01H 5/00

[52] U.S. Cl. ..... Plt./82.2

[58] Field of Search ..... Plt./74, 82.1, 82.2

[56] References Cited

U.S. PATENT DOCUMENTS

P.P. 6,240 8/1988 van der Knaap ..... Plt. 74

4,616,099 10/1986 Sparkes ..... 47/58

OTHER PUBLICATIONS

Broetjes et al, 1980. "A mutant of a mutant of a mutant of . . . Irradiation of a progressive radiation-induced mutants in a mutation breeding programme with *C. morifolium Ram.*". Euphytica 29:525-530.

Gosling, ed. 1979 *The Chrysanthenum Manual of the National Chrysanthemum Society. Essex Telegraph Press, Ltd. Colchester, England. pp. 329-336.*

Broertjes, et al, 1978, "Application of mutation breeding methods in the improvement of vegetatively propageed crops". Elsevier Sci., Pub. Co. New York. pp. 162-175.

Searle, et al, 1968 , *Chrysanthemums the Year Round.* Blandford Press, London, England, pp. 27-29, 320-327.

Chan. 1966, "Chrysanthemum and rose mutations induced by X-rays". Proc. Am. Soc. Hart. Sci. vol. 88:613-620.

Broertjes, 1966. "Mutation breeding of Chrysanthemums". Euphytica 15:156-162.

Dowrick et al, 1966. "The induction of mutations in Chrysanthemum using X- and gamma radiation". Euphytica 15:204-210.

*Primary Examiner*—Howard J. Locker

*Attorney, Agent, or Firm*—Burns, Doane, Swecker & Mathis

[57] ABSTRACT

A new and distinct cultivar of Chrysanthemum plant named Cream Daymark is provided. The new cultivar was the result of a mutation induced by controlled irradiation with x-rays and can be readily distinguished from the parent Daymark cultivar (U.S. Plant Pat. No. 6,240). More specifically, the new cultivar exhibits attractive light yellow or cream ray and disc florets which can be readily distinguished from the white blossom coloration of the parent cultivar. Also, the new cultivar has been found to exhibit a more compact growth habit with less vegetative growth and to exhibit a lesser plant height than the parent cultivar under the same growing conditions. The new cultivar is particularly suited for use in the production of a cut anemone spray.

1 Drawing Sheet

SUMMARY OF THE INVENTION

The present invention comprises a new and distinct cultivar of *Dendranthema morifolium* Ramat., and hereinafter is referred to by the cultivar name Cream Daymark.

The new cultivar is a mutation which was induced in a plant of the Daymark cultivar (U.S. Plant Pat. No. 6,240) by irradiation with x-rays at a level of 1750 rads. The discovery of the new cultivar was made at De Lier, The Netherlands, during August, 1985. As discussed hereafter, this discovery resulted in the identification of a single plant of the new cultivar.

It has been found that the new cultivar of the present invention:

(a) exhibits attractive light yellow ray and disc florets which can be distinguished from the white blossom coloration of the Daymark cultivar (U.S. Plant Pat. No. 6,240), and (b) exhibits a more compact growth habit with less vegetative growth and assumes a lesser plant height than the Daymark cultivar under the same growing conditions.

This combination of characteristics is capable of well distinguishing the new Cream Daymark cultivar from the parent Daymark cultivar and from all other known Chrysanthemum cultivars.

The new cultivar is particularly suited for use in the production of a cut anemone spray.

Asexual reproduction of the new cultivar by cuttings, as performed at De Lier, The Netherlands, has demonstrated that the characteristics of the new cultivar as herein disclosed are firmly fixed and are retained through successive generations of asexual propagation.

Cream Daymark has not been observed under all possible environmental conditions to date. Accordingly, it is possible that the phenotype may vary somewhat with variations in the environment, such as temperature, light, day length, contact with pesticides and/or subjection to growth retardant treatments.

In my companion application Ser. No. 07/577,696, filed concurrently herewith, entitled "Chrysanthemum Plant—Yellow Daymark Cultivar" is claimed a related cultivar in which the ray and disc florets exhibit a distinctive bright yellow coloration.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour chart of the Royal Horticultural Society, London, England. The color values were determined at 11:00 a.m. to 12:00 under natural daylight condition, at De Lier, The Netherlands.

Classification:

*Botanical.*—*Dendranthema morifolium* Ramat., cv. Cream Daymark.

*Commercial.*—Cut anemone spray.

INFLORESCENCE

A. Capitulum:

*Form.*—Flat.

*Type.*—Anemone.

*Diameter across face.*—Approximately 70 mm. on average.

*Diameter across disc.*—Approximately 26 mm. on average.

B. Corolla of ray and disc florets:

*Color(General tonality from a distance of one meter)*-.—Light yellow.

*Color ray (top surface).*—Approximates Yellow Group 5D.

*Color ray (under surface).*—Approximates Yellow Group 5D.

*Color (disc).*—Yellow-Green Group 145A changing to Yellow Group 4C.

Number of ray florets.—Approximately 30 on average.

*Number of ray florets.*—approximately 130 to 140 on average.

C. Reproductive organs:

*Androecium.*—Present in disc florets; numerous.

*Gynoecium.*—Present in both disc and ray florets; numerous.

PLANT

A. General appearance:

*Height.*—Approximately 80 cm. on average.

B. Foliage

*Color (upper surface).*—Yellow-Green Group 147A.

*Leaf size.*—Approximately 120×90 mm. on average.

*Branching laterals.*—Approximately 20 on average.

C. Response time:

The response time is approximately 8 weeks.

The plants of the new Cream Daymark cultivar can be distinguished from the parent Daymark cultivar (U.S. Plant Pat. No. 6,240) as well as its sister Yellow Daymark cultivar (Ser. No. 577,696, filed Sep. 5, 1990), both with respect to blossom coloration and other characteristics. The following data was obtained during November 1991 by a comparison of plants of the Daymark, Cream Daymark, and Yellow Daymark cultivars growing in a nursery at De Lier, The Netherlands.

| | DAYMARK Cultivar | CREAM DAYMARK Cultivar | YELLOW DAYMARK Cultivar |
|---|---|---|---|
| Ray Floret Coloration | White Group 155D | Yellow Group 5D | Yellow Group 3B |
| Disc Floret Coloration | Yellow-Green Group 145D changing to White Group 155A | Yellow-Green Group 145A changing to Yellow Group 4C | Yellow-Green Group 154C changing to Yellow Group 6C |
| Plant Height at Harvest Stage | 85–90 cm. | 80 cm. | 80–85 cm. |
| Number of Ray Forets (on average) | 25 | 30 | 34 |
| Number of Disc Florets (on average) | 110–120 | 130–140 | 140–150 |
| Flower Diameter | 75 mm. | 70 mm. | 70 mm. |
| Disc Diameter | 22 mm. | 26 mm. | 26 mm. |
| Number of Laterals (average) | 18 | 20 | 16 |
| Typical Leaf Size | 110 × 80 mm. | 120 × 90 mm. | 120 × 80 mm. |
| Foliage Coloration | Yellow-Green Group 147A | Yellow-Green Group 147A | Yellow-Green Group 147A |
| Response Time | 7½ weeks | 8 weeks | 8 weeks |

No clear distinctions with respect to petal shape and disease resistance have been observed to date with respect to the Daymark, Cream Daymark and Yellow Daymark cultivars.

I claim:

1. A new and distinct cultivar of Chrysanthemum plant named Cream Daymark, substantially as herein shown and described, which:

(a) exhibits attractive light yellow ray and disc florets which can be distinguished from the white blossom coloration of the Daymark cultivar (U.S. Plant Pat. No. 6,240), and (b) exhibits a more compact growth habit with less vegetative growth and assumes a lesser plant height than the Daymark cultivar under the same growing conditions.

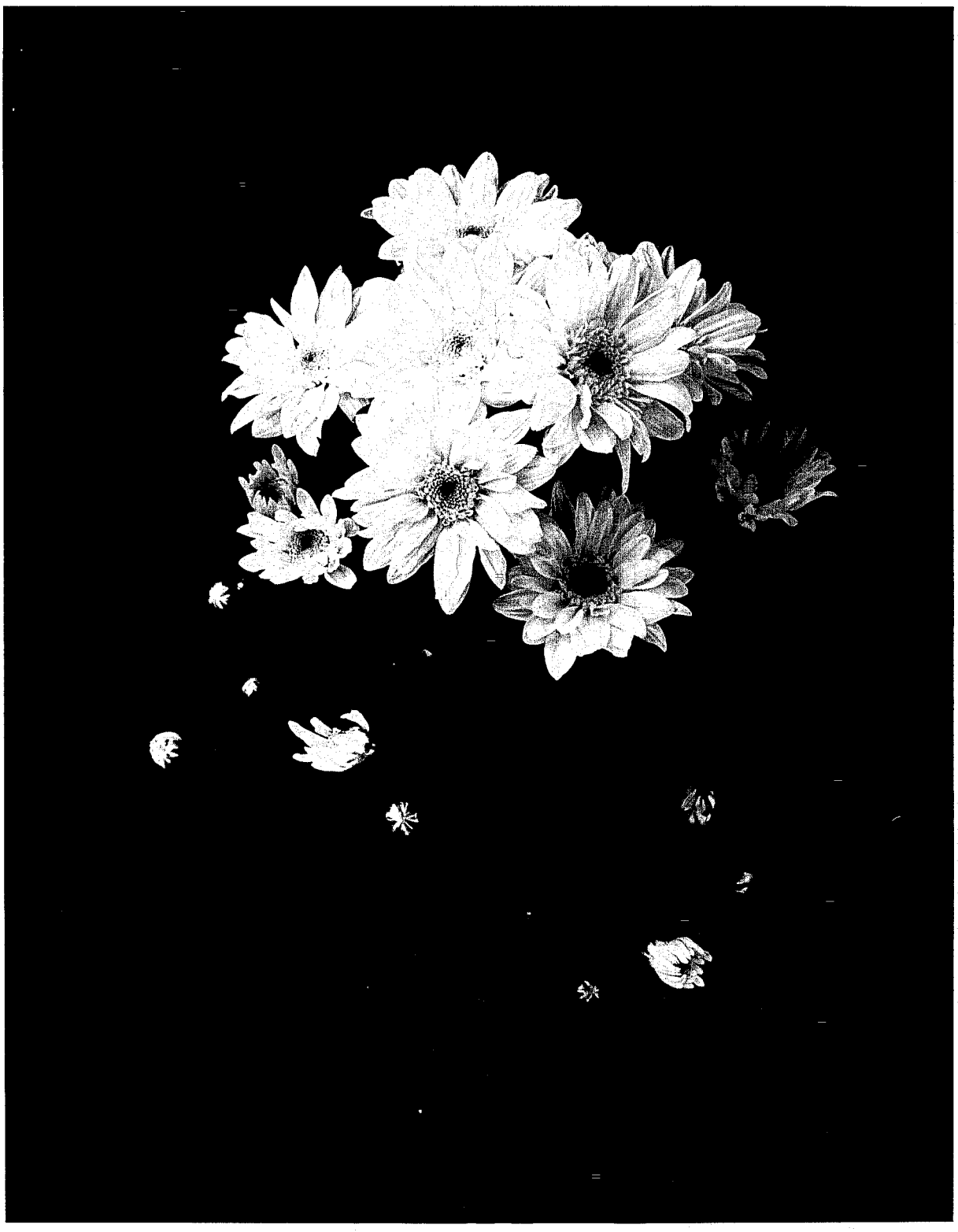

* * * * *